United States Patent [19]

Watt

[11] 4,194,501
[45] Mar. 25, 1980

[54] FIRST AID SPLINT FOR CERVICAL SPINE INJURIES

[76] Inventor: Russell A. Watt, 6393 Jadeite Ave., Alta Loma, Calif. 91701

[21] Appl. No.: 929,388

[22] Filed: Jul. 31, 1978

[51] Int. Cl.$^2$ ............................................. A61H 1/02
[52] U.S. Cl. ................................... 128/75; 128/87 B; 128/DIG. 20
[58] Field of Search ............... 128/DIG. 20, DIG. 23, 128/75, 78, 83, 84 R, 84 L, 85, 87 R, 87 B, 89 A, 89 R, 133, 134

[56] References Cited

U.S. PATENT DOCUMENTS

| Re. 27957 | 4/1974 | Larson | 128/89 R |
|---|---|---|---|
| 2,166,229 | 1/1937 | Anderson | 128/DIG. 23 |
| 2,772,675 | 12/1956 | Simmons | 128/87 B |
| 3,164,151 | 1/1965 | Nicoll | 128/75 |
| 3,336,922 | 8/1967 | Taylor | 128/75 |
| 3,343,532 | 9/1967 | Zumaglini | 128/75 |
| 3,662,750 | 5/1972 | Jorgensen | 128/75 |
| 3,669,102 | 6/1972 | Harris | 128/84 R |
| 3,957,040 | 5/1976 | Calabrese | 128/87 B |

FOREIGN PATENT DOCUMENTS

| 1276078 | 10/1961 | France | 128/75 |
|---|---|---|---|
| 467637 | 12/1951 | Italy | 128/DIG. 23 |
| 1319574 | 6/1973 | United Kingdom | 128/89 |
| 140162 | 12/1961 | U.S.S.R. | 128/75 |

OTHER PUBLICATIONS

Louis Yellin, Cervical Collar Ad., Journal of Bone & Joint Surgery, p. 43, Jan. 1951.
*Appliances for the Spine & Trunk*, Orthopaedics Appliances Atlas, 1952—p. 240.
*Kestler Traction Unit*, Ad. in Journal of Bone & Joint Surgery, 7/53, p. 42, vol. 35-A, #3.

*Primary Examiner*—Robert W. Michell
*Assistant Examiner*—Arthur S. Rose
*Attorney, Agent, or Firm*—Henri J. A. Charmasson

[57] ABSTRACT

A splint to be applied by a policeman, paramedic, or fireman during rescue operation to a suspected cervical spine injury victim. The splint is designed for quick on-site installation to immobilize the head and cervical area before any attempt is made to move the victim.

The splint is composed of two half sections. Each section is mounted on a shoulder harness and is designed to be fitted independently on either side of the head. The two sections are then connected to form a cage surrounding the victim's head. The head is secured within the cage by means of inflatable neck pillows. The splint may be fitted with an accessory designed to apply traction to the cervical vertebrae during emergency room treatment.

6 Claims, 9 Drawing Figures

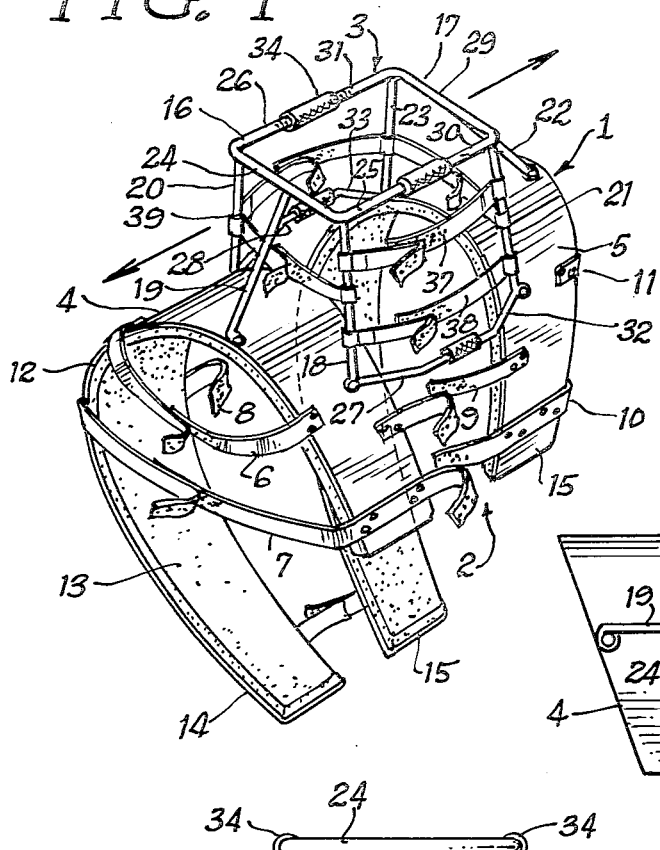
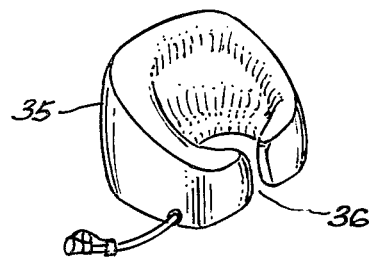
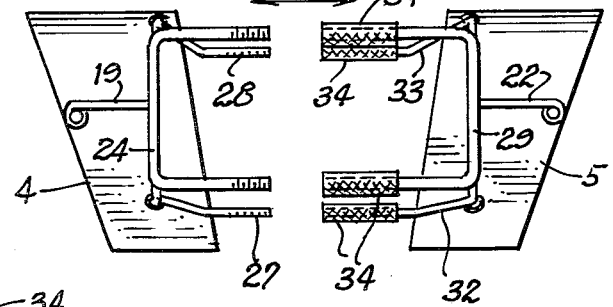
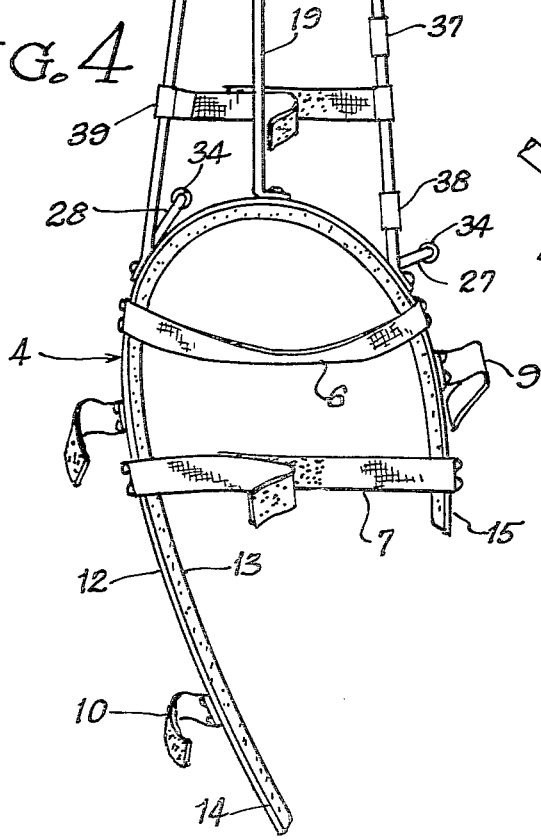
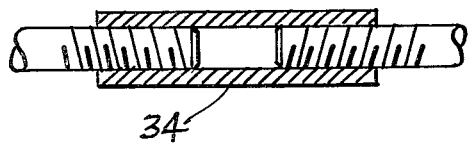

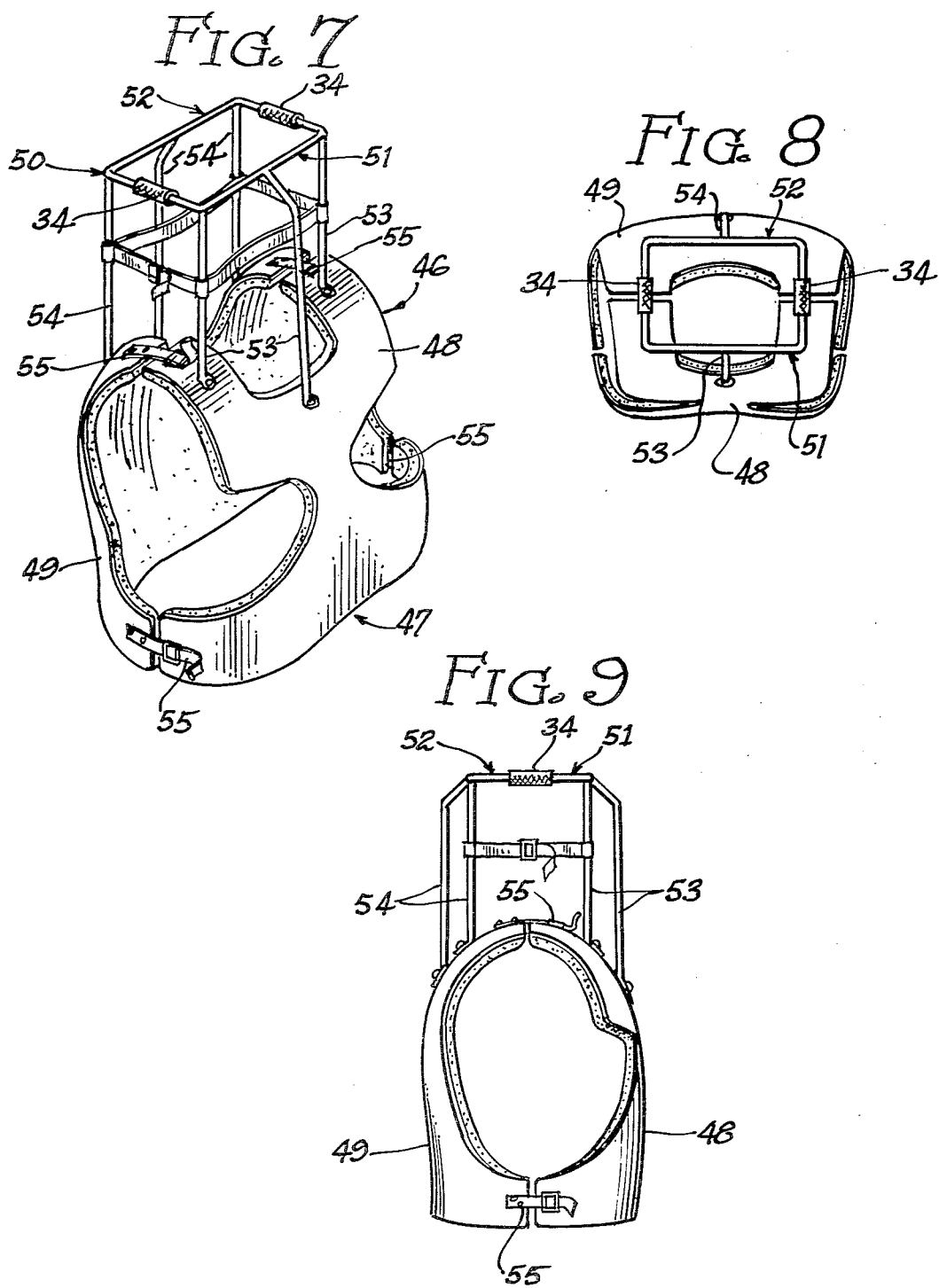

FIRST AID SPLINT FOR CERVICAL SPINE INJURIES

BACKGROUND OF THE INVENTION

It is imperative that the head of a suspected cervical fracture victim be immobilized before any attempt is made at moving the victim. Unrestricted movement of the head may cause serious damage to the spinal cord and result in quadraplegia. Yet such a victim may have to be extracted quickly from a burning wreckage after a collision or dragged away from a zone of danger before any first aid can be applied by trained personnel. Head brace and splints available to this date have been designed for therapeutic use and usually installed by an orthopedic surgeon in the controlled environment of a hospital. There is a need for a simple yet efficient device which could be installed quickly during rescue operatioons of a cervical spine injury victim by a policeman, fireman or paramedic.

Since traction may have to be applied to the cervical vertebrae of such victims, as part of the emergency room treatment, the splint should provide some means for this type of therapy.

SUMMARY OF THE INVENTION

This invention relates to orthopedic braces and splints designed to immobilize the head and neck of a cervical spine injury victim.

Its main purpose is to provide a simple splint which can be quickly and easily installed on a victim at the site of an accidient by a rescue team.

Another object of the invention is to provide a splint which can maintain the head and neck of the victim stationary in relation to the torso during emergency rescue and transportation.

A further object of the invention is to provide a device which can be used during emergency room treatment to apply therapeutic traction to the victim's cervical vertebrae.

IN THE DRAWING

FIG. 1 is a perspective view of a splint representing a first embodiment of the invention;

FIG. 2 is a perspective view of the inflatable pillow;

FIG. 3 is a top view of the splint illustrated in FIG. 1 showing the two half sections separated, and without the straps;

FIG. 4 is a right-side elevation view of the splint;

FIG. 5 is a perspective view of the traction device;

FIG. 6 is a cross-sectional view of one interlocking device;

FIG. 7 is a perspective view of a splint representing a second embodiment of the invention;

FIG. 8 is a top view of the splint shown in FIG. 7; and

FIG. 9 is a right-side elevational view thereof.

DESCRIPTION OF THE PREFERRED EMBODIMENT OF THE INVENTION

Referring now to FIGS. 1 through 6 of the drawing, there is shown a splint 1 for immobilizing the head of a cervical spine injury victim which comprises a body harness 2 surmounted by a head-cage 3. The body harness 2 comprises a right-shoulder pad 4, a left shoulder pad 5 and straps 6 through 11 for securing the shoulder pads to the victim's body. Each shoulder pad 4,5 comprises a hard top layer made of light metal alloy or plastic and a soft lining 13 underneath, made from cloth, rubber or other resilient material. Each shoulder pad 4, 5 has downward projection 14, 15 over the chest and back of the victim. Straps 6 through 11 are riveted to one of the projections 14, 15 and designed to circle the victim's body horizontally and to be fastened to the corresponding strap from the oppostie shoulder pad. The right shoulder pad 4 and associated straps 6 through 8 constitute a first half-section of the body harness 2 while the left-shoulder pad 5 and associated straps 9 through 11 constitute the second half-section.

The head cage 3 is constituted by two half-sections 16, 17 joined in the middle of the head cage 3. The right half-section 16 comprises three rigid members 18, 19 and 20, riveted at their base to the top layer 12 of the right-shoulder pad 4. These vertical members extend in a substantial vertical direction. They are joined at the top by a horizontal cross-member 24 which form the upper right, front-to-back edge of the head-cage 3. Projecting horizontally from the cross member 24, toward the left half section of the head cage are two half right-to-left cross-members 25, 26 forming one half of the upper front and back edges of the head-cage. Two additional horizontal cross members 27, 28 extend from the base of the front vertical member 18 and of the back vertical member 20 toward the half section 17.

The left half-section 17 of the head-cage 3 is a mirror image of the right half-section 16. The four half cross-members 25 through 28 of the right half-section 16 are conjunct to the four half-cross members 30 through 33 of the left half-section 17, along a vertical plane orthogonal to said half cross-members.

FIG. 6 illustrates the devices used to interlock each half cross-member to the corresponding half cross-member on the opposite section of the head cage.

The end of each half cross-members 25 through 28 and 30 through 33 is threaded externally to engage the inside thread of the interlocking sleeves 34.

The splint is used as follows. With the two halves of the body harness and head cage separated. Each shoulder pad 4, 5 is strapped on the victim's body the two halves 16,17 of the head-cage are interlocked by means of the four sleeves 34.

An inflatable pillow 35 made of rubber, plastic or the like having the approximate inflated shape of an open toroid shown in FIG. 2 is designed to be wrapped around the victim's neck. The pillow is installed in the deflated state with the open area 36 in front of the victim's throat. The pillow 35 is then inflated until it occupies the area between the victim's neck and the head-cage members 18 through 23 and half cross-members 27, 28 and 32,33. The pillow 35 thus exerts gentle pressure against the neck and lower part of the victim's skull immobilizing the head within the confines of the head-cage 3. The straps 6 through 11 illustrated by the drawing are of the self-connecting type such as those manufactured under the VELCRO trade mark.

Additional straps 37, 38, 39 may also be used between the vertical members 18, 20, 21, 23 of the head-cage ot provide additional support for the victim's head.

FIG. 5 illustrates a device used in conjunction with the head-cage for applying traction to the cervical vertebrae of the victim. The traction device 40 comprised two rollers 41,42 rotating around a shaft 43. The shaft is mounted from side to side across the top of the head-cage 3. Each end of the shaft 43 is welded orthogonally to a semi-circular supporting bracket 44 resting on top of the two top front-to-back cross-members 24,29 of the head-cage 40.

The rollers 41,42 are controlled by an internal ratchet mechanism which allows rotation in only one direction.

Straps 45 wound around the rollers 41, 42 are used to pull up the victim's head in order to exert traction upon the injured cervical vertebrae.

The straps 45 can be attached to the head by way of a neck brace or skull ring secured to the head by skull pin as is commonly done in modern therapeutic traction devices.

A second embodiment 46 of the invention is illustrated in FIGS. 7 through 9.

In this version of the splint, the body harness 47 comprises a pectoral plate 48 shaped to wrap around the chest of the patient, forming a first half-section of the harness. The second half-section is constituted by a dorsal plate 49 designed to cover the back of the victim.

The head-cage 50 is made of a frontal part 51 and a back part 52 conjunct by means of the secure interlocking devices 34 described in the first embodiment of the invention.

A set of three vertical members 53 extend from the pectoral plate 48 in front of the victim's face. A second set of three vertical members 54, extend from the dorsal plate 49 behind the neck of the victim. The structure of the head cage 50 is substantially similar to the one described above in the first embodiment of the invention but as if shifted ninety degrees around the victim's head.

The two half-sections of the harness are fastened together by means of buckling straps 55 located on the shoulder and under the arms of the victim. An air pillow similar to the one illustrated in FIG. 2 is used to immobilize the victim's head within the head-cage 50. Other equivalent means may be used to secure the body harness to the victim's torso such as straps circumcincturing the torso or the like.

While I have shown and described the preferred forms of the present invention and have suggested modifications therein, other changes may be made within the scope of the appended claims.

I claim:

1. A device for immobilizing the head and cervical spine of an injury victim which comprises:
    a body harness having first and second half sections, means for releasibly connecting said half sections together,
    said body harness being adopted to embrace the thoracic region, the shoulders, the sides and the back of a victim,
    a head cage comprising a first and second pair of elongated rigid members and first and second U shaped members,
    said first pair being mounted on said first half section in spaced relationship such that said first pair of rigid members projects substantially upward around the head of a victim when said harness is worn by a victim,
    said second pair being mounted on said second half section in spaced relation such that said second pair of rigid members project substantially upward around the head of a victim when said harness is worn by a victim,
    said first U shaped member being mounted horizontally on said first pair of rigid members,
    said second U shaped member being mounted horizontally on said second pair of rigid members,
    said U shaped members being sized and positioned such that they extend completely around the head of a victim when said harness is worn by a victim,
    means for releasibly connecting the ends of the U shaped members together,
    said head cage further comprising an inflatable air pillow shaped like an open toroid insertable within said first and second pair of rigid members such that when said harness is worn said pillow is positioned between said rigid members and the neck of a victim and when inflated said pillow immobilizes the head of a victim within the confines of said rigid members by encircling the neck of a victim.

2. The device claimed in 1 wherein each said half-section comprises a shoulder pad and means for securing the shoulder pad to a victim's body.

3. The device claimed in 1 wherein the first half-section comprises a pectoral plate and the second half-section comprises a dorsal plate; and which further comprises means for securing each half-section to the other half section and to the body of a victim.

4. The device claimed in claim 1 which further comprises means secured to the upper part of the head cage for applying upward tension to the victim's head; and
    said tension mechanism comprising at least one ratchet controlled roller rotating around a horizontal shaft, said shaft extending from side to side across the top of the head cage, and having at each end an orthogonally mounted supporting bracket resting on top of one of said cross members.

5. The device claimed in claim 1 wherein each half section comprises interlocking means for disassembly in direct alignment with the coronal plane of a human body.

6. The device claimed in claim 1 wherein each half section comprises interlocking means for disassembly in direct alignment with the sagittal plane of a human body.

* * * * *